United States Patent
Zhang et al.

(10) Patent No.: US 9,676,725 B2
(45) Date of Patent: Jun. 13, 2017

(54) S-CRYSTAL FORM OF IVABRADINE HYDROCHLORIDE, AND PREPARATION METHOD AND PHARMACEUTICAL COMPOSITION THEREOF

(71) Applicant: Beijing Lunarsun Pharmaceutical Co., LTD., Chaoyang District, Beijing (CN)

(72) Inventors: Xiaobo Zhang, Beijing (CN); Dongdong Cui, Beijing (CN); Tianxiang Zhang, Beijing (CN)

(73) Assignee: Beijing Lunarsun Pharmaceutical Co., LTD., Beijing (CN)

( * ) Notice: Subject to any disclaimer, the term of this patent is extended or adjusted under 35 U.S.C. 154(b) by 0 days.

(21) Appl. No.: 15/107,406

(22) PCT Filed: Sep. 25, 2014

(86) PCT No.: PCT/CN2014/087405
§ 371 (c)(1),
(2) Date: Jun. 22, 2016

(87) PCT Pub. No.: WO2015/101072
PCT Pub. Date: Jul. 9, 2015

(65) Prior Publication Data
US 2017/0044108 A1 Feb. 16, 2017

(30) Foreign Application Priority Data

Jan. 6, 2014 (CN) .......................... 2014 1 0008691

(51) Int. Cl.
*C07D 223/16* (2006.01)
*A61K 31/55* (2006.01)
*A61K 9/20* (2006.01)

(52) U.S. Cl.
CPC .......... *C07D 223/16* (2013.01); *A61K 9/2054* (2013.01); *A61K 31/55* (2013.01); *C07B 2200/13* (2013.01)

(58) Field of Classification Search
CPC .................................................. C07D 223/16
See application file for complete search history.

(56) References Cited

U.S. PATENT DOCUMENTS 5,296,482 A 3/1994 Peglion et al.

FOREIGN PATENT DOCUMENTS

| CN | 101284813 A | 10/2008 |
| CN | 101805289 A | 8/2010 |
| CN | 103012269 A | 4/2013 |
| CN | 103183639 A | 7/2013 |
| CN | 103864690 A | 6/2014 |
| WO | 2008/146308 A2 | 12/2008 |
| WO | 2012/025940 A1 | 3/2012 |
| WO | 2013/064427 A1 | 5/2013 |

OTHER PUBLICATIONS

Chinese Office Action, Application No. 201410008691.X dated Sep. 7, 2015.
PCT International Search Report, Application No. PCT/CN2014/087405 filed Sep. 25, 2014, dated Jan. 5, 2015.

*Primary Examiner* — Bruck Kifle
(74) *Attorney, Agent, or Firm* — MacMillan, Sobanski & Todd, LLC

(57) ABSTRACT

Disclosed are a new S crystal form of ivabradine hydrochloride, and preparation method and pharmaceutical composition thereof. The S crystal form of ivabradine hydrochloride has a powder diffraction pattern having characteristic peaks at degrees two-theta positions of 8.5±0.2, 11.5±0.2, 14.6±0.2, 15.3±0.2, 16.1±0.2, 17.1±0.2, 17.4±0.2, 17.8±0.2, 18.6±0.2, 19.3±0.2, 21.6±0.2, 21.9±0.2, 27.2±0.2, and, by DSC measurement, has an endothermic crystal transformation peak as a characteristic peak at 111.6° C. and an exothermic crystal transformation peak as a characteristic peak at 136.9° C., and a melting decomposition peak as a characteristic peak at 194.9° C. The S crystal form products are easy to dry, have high purity and stability, and are convenient for long-term storage without particular temperature and humidity requirements. The preparation method thereof facilitates industrial production, and has great application value and market value.

7 Claims, 2 Drawing Sheets

S-CRYSTAL FORM OF IVABRADINE HYDROCHLORIDE, AND PREPARATION METHOD AND PHARMACEUTICAL COMPOSITION THEREOF

This is a national stage application filed under 35 U.S.C. §371 of international application PCT/CN2014/087405, filed under the authority of the Patent Cooperation Treaty on Sep. 25, 2014, published; which claims the benefit of Patent Application No. CN 2014-10008691.X, filed on Jan. 6, 2014. The entire disclosures of all the aforementioned applications are expressly incorporated herein by reference for all purposes.

TECHNICAL FIELD

The present invention relates to an S crystal form of ivabradine hydrochloride, its preparation method and a pharmaceutical composition comprising the compound as an active ingredient.

BACKGROUND ART

Ivabradine hydrochloride has a chemical name of 3-{3-[{[(7S)-3, 4-dimethoxybicyclo[4.2.0]octa-1,3,5-trien-7-yl]-methyl}(methyl)-amino]propyl}-7,8-dimethoxy-1,3,4,5-tetrahydro-2H-3-benzazepin-2-one hydrochloride, CAS No. 148849-67-6, and a structural formula as Formula I:

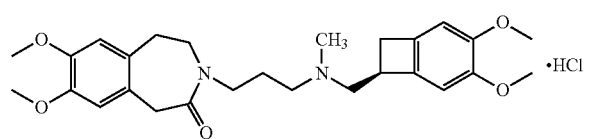

Ivabradine hydrochloride is the first selective and specific cardiac pacemaker current inhibitor as developed by Servier Company of France, and this product is approved by the European Agency for the Evaluation of Medicinal Products (EMEA) in August 2005 to be marketed in 27 countries in Europe for treatment of chronic stable angina companied with normal sinus rhythm, taboo or intolerance on B receptor blocker, especially supraventricular arhythmicity or cardiac failure.

European Patent EP0534859 first reports the preparation methods and medical uses of ivabradine and its pharmaceutically acceptable addiction salts with acids, especially hydrochloride. Due to excellent pharmaceutical value of ivabradine hydrochloride, a lot of crystal forms of ivabradine hydrochloride have been reported in the prior art.

US20070082887A1 discloses an α crystal form of ivabradine hydrochloride, which is prepared using toluene/methyl-pyrrolidinone as solvent, and its crystal powder diffraction pattern has characteristic peaks at degrees two-theta positions of about 4.1, 7.7, 8.1, 10.4, 16.5, 17.4, 20.2, 21.9, 25.7 and 26.5.

EP1695965A1 discloses a β crystal form of ivabradine hydrochloride, which is prepared by dissolving ivabradine hydrochloride in water at 74° C. and crystallizing at room temperature for 2 days, and its crystal powder diffraction pattern has characteristic peaks at degrees two-theta positions of about 9.2, 16.9, 18.4, 18.8, 19.7, 21.3, 21.6, 22.6, 23.0 and 25.3.

EP1695710A1 discloses a βd crystal form of ivabradine hydrochloride, which is prepared by dissolving ivabradine hydrochloride in water at 74° C. and crystallizing at room temperature for 2 days, and its crystal powder diffraction pattern has characteristic peaks at degrees two-theta positions of about 9.2, 12.5, 13.6, 16.0, 17.3, 19.6, 20.4, 22.3 and 25.0.

US20060194963A1 discloses a γ crystal form of ivabradine hydrochloride, which is prepared by dissolving ivabradine hydrochloride in 2-oxyethanol under refluxing, crystallizing at room temperature for 8 days, filtering, and washing with cyclohexane, and its crystal powder diffraction pattern has characteristic peaks at degrees two-theta positions of about 4.2, 12.5, 13.4, 17.0, 21.5, 13.4, 17.0, 21.1, 24.2, 24.5, 26.4 and 28.0.

EP1695709A1 discloses a γd crystal form of ivabradine hydrochloride, which is prepared by dissolving ivabradine hydrochloride in 2-oxyethanol under refluxing, and its crystal powder diffraction pattern has characteristic peaks at degrees two-theta positions of about 4.3, 12.5, 13.4, 15.8, 16.9, 18.9, 20.9, 24.1, 24.4 and 26.2.

US20070082885A1 discloses a δ crystal form of ivabradine hydrochloride, which is prepared by dissolving ivabradine hydrochloride in acetonitrile at 70° C., standing for 2 days and crystallizing at room temperature, and its crystal powder diffraction pattern has characteristic peaks at degrees two-theta positions of about 4.1, 10.9, 14.7, 15.3, 16.3, 16.8, 17.9, 19.2, 21.7, 22.2, 23.1, 24.8, 25.2, 25.6, 26.7 and 27.6.

US20070082886A1 discloses a δd crystal form of ivabradine hydrochloride, which is prepared by dissolving ivabradine hydrochloride in acetonitrile at 70° C., standing for 2 days and crystallizing at room temperature, filtering under vacuum, spreading on crystallizing pan, and drying at 85° C., and its crystal powder diffraction pattern has characteristic peaks at degrees two-theta positions of about 8.6, 14.6, 15.3, 17.2, 18.1, 21.4, 22.1, 22.5, 23.9, 26.2, 26.9 and 27.6.

WO2011098582A1 discloses Z, X and K crystal forms of ivabradine hydrochloride, which are prepared by dissolving amorphous salt in isopropanol and crystallizing at 22° C., or by salifying ivabradine free alkali with concentrated hydrochloric acid in isopropanol and crystallizing at 2° C., in which the resultant solid without drying is Z crystal form, the Z crystal form is dried under vacuum at 22° C. for 2 h to obtain X crystal form, and Z crystal form is dried under vacuum at 70° C. for 2 h to obtain K crystal form; the crystal powder diffraction pattern of Z crystal form has characteristic peaks at degrees two-theta positions of about 3.9, 15.1, 16.2, 16.6, 17.8, 19.0, 22.0, and 24.7; the crystal powder diffraction pattern of X crystal form has characteristic peaks at degrees two-theta positions of about 11.0, 16.5, 16.9, 21.8, 22.4, 23.7, 26.0, and 27.9; the crystal powder diffraction pattern of K crystal form has characteristic peaks at degrees two-theta positions of about 8.6, 14.6, 17.2, 18.3, 21.6, 22.3, 24.0, and 26.4.

WO2012025940A1 discloses a Zeta-crystal form, which is prepared by recrystallizing ivabradine hydrochloride in acetonitrile, and removing the organic solvent from solid by drying under controlled humidity, and its crystal powder diffraction pattern has characteristic peaks at degrees two-theta positions of about 11.0, 14.5, 16.5, 16.8, 22.2, 23.5, 25.9, 27.6, 28.9, 30.7 and 34.1.

WO2008125006A1 discloses a new crystal form of ivabradine hydrochloride, which is prepared by recrystallizing ivabradine hydrochloride in butanone (or methyl-pyrrolidinone/ethyl acetate), and drying under vacuum at 60-70° C., and its crystal powder diffraction pattern has characteristic peaks at degrees two-theta positions of about 4.02, 7.69, 8.03, 10.37, 11.81, 13.10, 13.72, 16.41, 17.32, 18.12, 20.02, 20.52, 21.30, 21.86, 22.28, 25.72, 26.42, 26.74 and 28.38.

CN101768117A discloses a W-crystal form of ivabradine hydrochloride, which is prepared by dissolving ivabradine hydrochloride in acetone/methanol under refluxing, standing and crystallizing, filtering, and drying solid under vacuum at 85° C., and its crystal powder diffraction pattern has characteristic peaks at degrees two-theta positions of about 4.1, 9.1, 14.6, 17.2, 18.2, 23.4, 25.4 and 37.7.

CN101805289A discloses a ω-crystal form of ivabradine hydrochloride and a preparation method thereof, in which ivabradine hydrochloride is dissolved in water and then freeze-dried, and its crystal powder diffraction pattern has characteristic peaks at degrees two-theta positions of about 6.6, 9.1, 14.8, 16.8, 18.2, 18.4, 19.6, 21.2, 21.5, 22.5, 23.1, 23.7, 25.3 and 27.4.

CN103012269A discloses a C-crystal form of ivabradine hydrochloride and a preparation method thereof, in which ivabradine hydrochloride is dissolved in ethanol, added with ethyl acetate and crystallized, filtered to collect product, and its crystal powder diffraction pattern has characteristic peaks at degrees two-theta positions of about 7.9, 8.3, 9.4, 10.7, 12.1, 14.1, 16.7, 17.6, 18.5, 20.4, 21.6, 22.2, 26.0 and 26.7.

WO2008065681A2 discloses a Form-I crystal form of ivabradine hydrochloride, which is prepared by using ivabradine free alkali in HCl/acetonitrile, and its crystal powder diffraction pattern has characteristic peaks at degrees two-theta positions of about 8.6, 9.1, 11.2, 11.7, 14.6, 15.3, 17.2, 18.2, 19.6, 20.3, 21.0, 21.5, 22.2, 22.7, 23.9, 26.4, 27.0 and 29.4.

WO2013102929 discloses Form-II and Form-III crystal forms of ivabradine hydrochloride, wherein ivabradine hydrochloride is dissolved in methyl ethyl ketone/tetrahydrofuran mixture solvents, cooled and crystallized, the product is dried at 40-45° C. under vacuum for 12 h to obtain Form-II crystal, and its crystal powder diffraction pattern has characteristic peaks at degrees two-theta positions of about 11.0, 14.5, 16.5, 16.8, 22.2, 23.5, 25.9, 27.6, 28.9, 30.7, 34.08; or ivabradine hydrochloride is dissolved in methyl ethyl ketone, cooled and crystallized, the product is dried at 40-45° C. under vacuum for 12 h to obtain Form-III crystal, and its crystal powder diffraction pattern has characteristic peaks at degrees two-theta positions of about 15.48, 16.18, 19.00, 19.78, 24.12 and 24.41.

WO2013064307A1 discloses Form-IV crystal form of ivabradine hydrochloride, which is prepared by pulping ivabradine hydrochloride in toluene, ethanol, acetone, methyl ethyl ketone, methyl isobutyl ketone, ethyl acetate, isopropyl acetate or their mixture solvents, and drying at 45° C. under vacuum, and its crystal powder diffraction pattern has characteristic peaks at degrees two-theta positions of about 8.11, 8.74, 15.55, 17.17, 19.18, 19.89, 21.82, 22.49, 24.29 and 24.53.

At present, the first-researching manufacturer uses α crystal form of ivabradine hydrochloride as the crystal form for preparation. Although α crystal form has good stability, toluene/methyl-pyrrolidinone are used as solvents during its preparation. As these two solvents (especially methyl-pyrrolidinone) have high boiling points, the residual solvent in product can hardly be removed, and high-temperature and long-term baking are usually necessary to reach the standard. However, such baking procedure may readily lead to poor purity of the product, thereby influencing the quality of the preparation.

It is well known that a stable crystal form has small entropy, high melting point, and good chemical stability, but has a poor dissolution rate and solubility, and thus has a poor bioavailability; on the contrary, an unstable crystal form has opposite values; while a metastable crystal form has moderate values, wherein its stability is slightly inferior to the stable crystal form, but its dissolubility and bioavailability are better than those of the stable crystal form. Hence, many manufacturers make efforts to find metastable crystal forms with excellent dissolubility and bioavailability as well as relatively good stability. Although many crystal forms have been reported in the documents, their stability and preparation methods are not satisfied. For example, the δd crystal form reported by the first-researching manufacturer may continuously transform into α crystal form at room temperature; and DSC test reveals that crystal form transformation occurs at 120° C., and its endothermic peak and exothermic peak during transformation is very small, that is, relevant peaks are not obvious, which means that after 10 days storage at room temperature, most of the δd crystal form will transform into α crystal form. Delta crystal form contains acetonitrile which can hardly be removed, and it is difficult to distinguish from acetonitrile-containing crystal form. In addition, ivabradine hydrochloride as a hydrochloride is very easy to absorb moisture, while the change of water content may result in changes of many crystal forms, for example, the change between γd and γ, the change between βd and β.

In sum, it still is a goal for many manufacturers to find a new crystal form with good stability, and which not only is very easy to be produced in an industrial scale, easy to dry, has a high purity, but also has high stability, can be stored for long-term without special requirements in terms of temperature, moisture and so on.

After massive screening by using different crystal forms or amorphous form of ivabradine hydrochloride as initial raw material, using a serious of conventional solvents and their mixture solvents as solvents for crystallization and transformation, controlling transformation time, transformation temperature and drying conditions, and performing many experiments for crystallization and transformation, the inventors surprisingly found that a new S crystal form could be prepared by performing transformation of δd and δ crystal forms as reported in documents in tetrahydrofuran for a long time. DSC tests revealed that the S crystal form has obvious crystal type transform peak, indicating that this crystal form has good stability. High-temperature tests and moisture tests confirm that the S crystal form has good stability and does not change even if water content reaches 3%. Thus, it is suitable for conventional storage. In addition, the used transformation solvent, tetrahydrofuran, is easy to be removed, so the purity of the product does not change during drying procedure, it is suitable for preparing a product with high purity.

Contents of the Invention

The object of the present invention is to provide an S crystal form of ivabradine hydrochloride; the crystal form is different from any one in the prior art, has good stability in term of temperature and moisture; is produced by using conventional solvents with a low-boiling point and thus is easy to dry; has good stability in term of water absorption and thus is suitable for long-term storage. The S crystal form of ivabradine hydrochloride has a powder diffraction pattern as shown in FIG. 1 and a DSC thermogram as shown in FIG. 2.

The powder diffraction is measured by using X'Pert PRO MPD multifunction powder diffractometer of PANalytical Company of the Netherlands, and using Cu-Kα radiation to obtain the powder diffraction spectrum as shown in FIG. 1, in which the parameters of characteristic peaks are shown in Table 1.

TABLE 1

Parameters of characteristic peaks of the powder diffraction pattern of the S crystal form of ivabradine hydrochloride of the present invention

| Pos. [°2Th.] | Height [cts] | FWHM [°2Th.] | d-spacing [Å] | Rel. Int. [%] |
|---|---|---|---|---|
| 4.3926 | 994.01 | 0.1948 | 20.11677 | 20.52 |
| 8.5434 | 2161.1 | 0.1624 | 10.35011 | 44.61 |
| 9.7725 | 615.82 | 0.3897 | 9.05087 | 12.71 |
| 11.4983 | 1623.5 | 0.1299 | 7.69602 | 33.51 |
| 13.2929 | 591.27 | 0.2273 | 6.66079 | 12.21 |
| 14.6473 | 3184.22 | 0.2273 | 6.04778 | 65.73 |
| 15.2836 | 2359.15 | 0.1624 | 5.79742 | 48.7 |
| 16.0819 | 3654.37 | 0.2273 | 5.51139 | 75.44 |
| 17.1331 | 4844.11 | 0.1948 | 5.17553 | 100.00 |
| 17.4563 | 1933.35 | 0.0974 | 5.08044 | 39.91 |
| 17.8164 | 2430.20 | 0.1624 | 4.97855 | 50.17 |
| 18.5509 | 1880.80 | 0.1948 | 4.78305 | 38.83 |
| 19.2562 | 1178.33 | 0.1624 | 4.60943 | 24.33 |
| 20.5935 | 1456.16 | 0.1624 | 4.31301 | 30.06 |
| 21.5669 | 2647.53 | 0.2273 | 4.12050 | 54.65 |
| 21.9538 | 3375.43 | 0.1624 | 4.04876 | 69.68 |
| 22.4793 | 1166.53 | 0.1948 | 3.95528 | 24.08 |
| 23.3198 | 1751.13 | 0.3247 | 3.81459 | 36.15 |
| 24.2556 | 1578.95 | 0.1624 | 3.66951 | 32.60 |
| 24.9125 | 1259.66 | 0.1948 | 3.57421 | 26.00 |
| 26.6075 | 1411.25 | 0.1948 | 3.35024 | 29.13 |
| 27.2281 | 1984.47 | 0.2273 | 3.27528 | 40.97 |
| 27.9733 | 1156.18 | 0.1624 | 3.18970 | 23.87 |
| 28.5810 | 772.01 | 0.1624 | 3.12324 | 15.94 |
| 29.5716 | 848.81 | 0.1299 | 3.02084 | 17.52 |
| 30.3051 | 505.59 | 0.2273 | 2.94938 | 10.44 |
| 31.5730 | 312.00 | 0.2922 | 2.83377 | 6.44 |
| 32.6957 | 376.55 | 0.3897 | 2.73899 | 7.77 |
| 33.8867 | 404.32 | 0.3897 | 2.64540 | 8.35 |
| 36.1196 | 280.97 | 0.3897 | 2.48682 | 5.80 |
| 38.2875 | 228.13 | 0.2598 | 2.35085 | 4.71 |
| 39.0999 | 180.88 | 0.1948 | 2.30386 | 3.73 |

In DSC and TG tests, the used instruments are DSC-204, and STA-409. The conditions for DSC test are as following: the temperature is 14-250° C., the heating rate is 10.0 K/min; the conditions for TG test are as following: the temperature is 20-250° C., the heating rate is 10.0 K/min.

The results of DSC test are shown in FIG. 2, and the DSC test indicates that the obtained S crystal form of ivabradine hydrochloride has crystal type transformation peaks including an endothermic characteristic peak at 111.6±1° C. and an exothermic characteristic peak at 136.9±1° C., and has a melting decomposition peak at 194±1° C.

The results of TG test are shown in FIG. 3, and the TG test further indicates the obtained S crystal form of ivabradine hydrochloride gradually starts to lose adsorbed water at a low temperature (about 60° C.). Compared with DSC thermogram, it's confirmed that the DSC thermogram has crystal type transformation peaks including an endothermic characteristic peak at 111.6±1° C. and an exothermic characteristic peak at 136.9±1° C., and has an endothermic peak at 194±1° C. as melting decomposition peak.

The present invention provides an S crystal form of ivabradine hydrochloride, characterized in that the S crystal form of ivabradine hydrochloride has a powder diffraction pattern having characteristic peaks at degrees two-theta positions of 8.5±0.2, 11.5±0.2, 14.6±0.2, 15.3±0.2, 16.1±0.2, 17.1±0.2, 17.5±0.2, 17.8±0.2, 18.6±0.2, 19.3±0.2, 21.6±0.2, 21.9±0.2, and 27.2±0.2.

The present invention provides an S crystal form of ivabradine hydrochloride, the powder diffraction pattern thereof has characteristic peaks and relative intensities as shown in the following table.

TABLE 2

Characteristic peaks and relative intensities thereof in the powder diffraction pattern of the S crystal form of ivabradine hydrochloride of the present invention

| Pos. [°2Th.] ± 0.2 | Rel. Int. [%] |
|---|---|
| 8.5 | 44.61 |
| 11.5 | 33.51 |
| 14.6 | 65.73 |
| 15.3 | 48.70 |
| 16.1 | 75.44 |
| 17.1 | 100.00 |
| 17.5 | 39.91 |
| 17.8 | 50.17 |
| 18.6 | 38.83 |
| 19.3 | 24.33 |
| 21.6 | 54.65 |
| 21.9 | 69.68 |
| 27.2 | 40.97 |

Another object of the present invention is to provide a method for preparing an S crystal form of ivabradine hydrochloride, comprising performing crystal type transformation by stirring a crystal form of ivabradine hydrochloride or an amorphous form of ivabradine hydrochloride in tetrahydrofuran for a long time, and filtering and collecting, drying under a reduced pressure to obtain the S crystal form of ivabradine hydrochloride. The crystal form of ivabradine hydrochloride is preferably δ crystal form or δd crystal form of ivabradine hydrochloride. The ratio of mass (g) of the crystal form of ivabradine hydrochloride or amorphous form of ivabradine hydrochloride to volume (ml) of tetrahydrofuran is 1:10 (g/ml), preferably 1:3 to 1:6 (g/ml). The stirring is performed at a temperature of 0-50° C., preferably 25-30° C., and the stirring is performed for 6-72 h, preferably 12-24 h.

Further another object of the present invention is to provide a pharmaceutical composition comprising the compound as an active ingredient, which can be used as a medicament for treatment or prevention of angina, myocardial infarction and relevant arhythmicity.

SPECIFIC MODEL FOR CARRYING OUT THE INVENTION

Example 1

1 kg of ivabradine hydrochloride was placed in a 50 L reactor, added with 20 L of acetonitrile, heated for dissolution under refluxing, and then stirring for 30 min, naturally cooled to reach room temperature, crystallized at room temperature for 4 h, then filtered to collect wet product, and the wet product was identified as δ crystal form by powder diffraction measurement.

The above wet product was placed in 5 L of tetrahydrofuran, controlled to have an internal temperature of 25-30°

C., stirred to performed crystal type transformation for 24 h, the product was filtered out and collected, dried under a reduced pressure at 50° C. for 24 h to obtain 950 g product with a yield of 95%.

The product purity was measured as 99.82%; the content of the maximum single impurity was 0.03%; the moisture content was 0.46%; the contents of residual solvents were as following: acetonitrile was not detected; the content of the residual THF was 0.001%.

The obtained S crystal form of ivabradine hydrochloride was subjected to powder diffraction analysis, differential thermal analysis, and thermo-gravimetric analysis.

Figure 1:
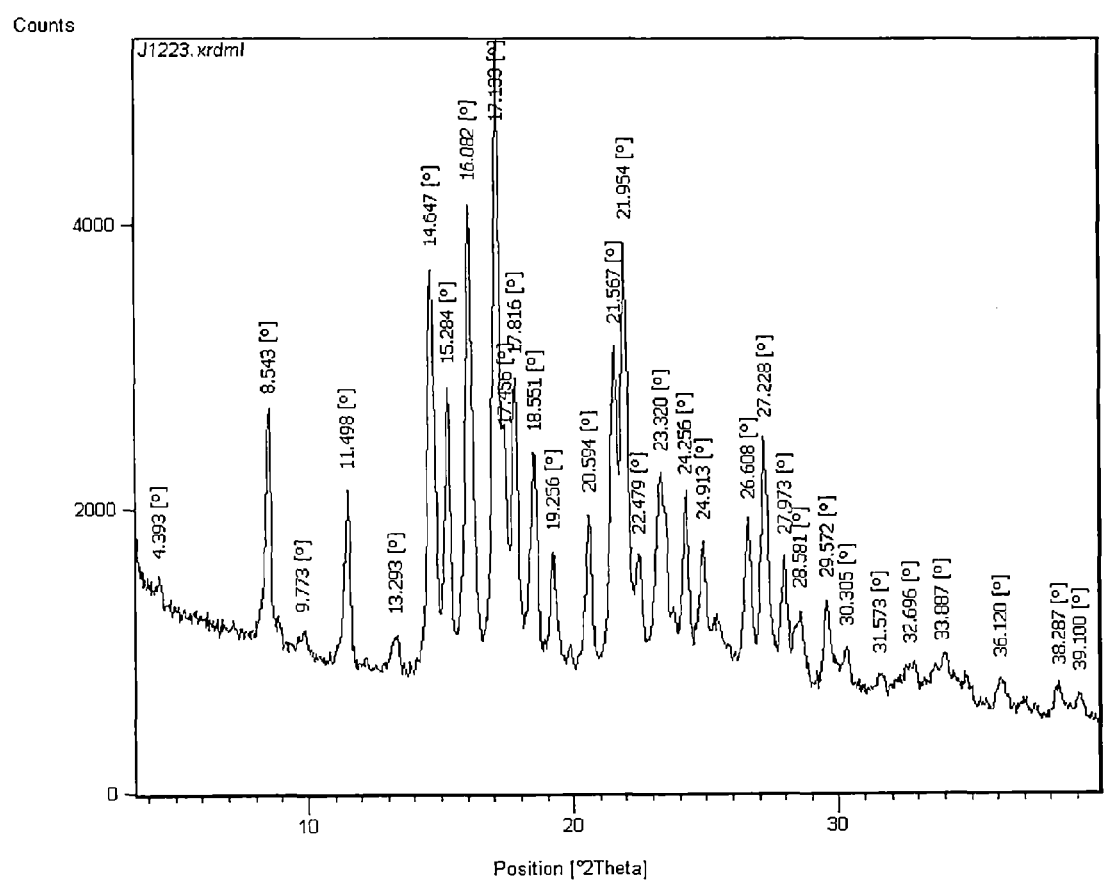
FIG. 1 shows an X-ray powder diffraction pattern of S crystal form of ivabradine hydrochloride.

The powder diffraction was measured by using X'Pert PRO MPD multifunction powder diffractometer of PANalytical Company of the Netherlands, and using Cu-Ka radiation to obtain the powder diffraction pattern shown in FIG. 1, in which the parameters of characteristic peaks were shown in Table 1.

In DSC and TG tests, the used instruments were DSC-204, STA-409. The conditions for DSC test were as following: the temperature was 14-250° C., the heating rate was 10.0 K/min; the conditions for TG test were as following: the temperature was 20-250° C., the heating rate was 10.0 K/min.

Figure 2:
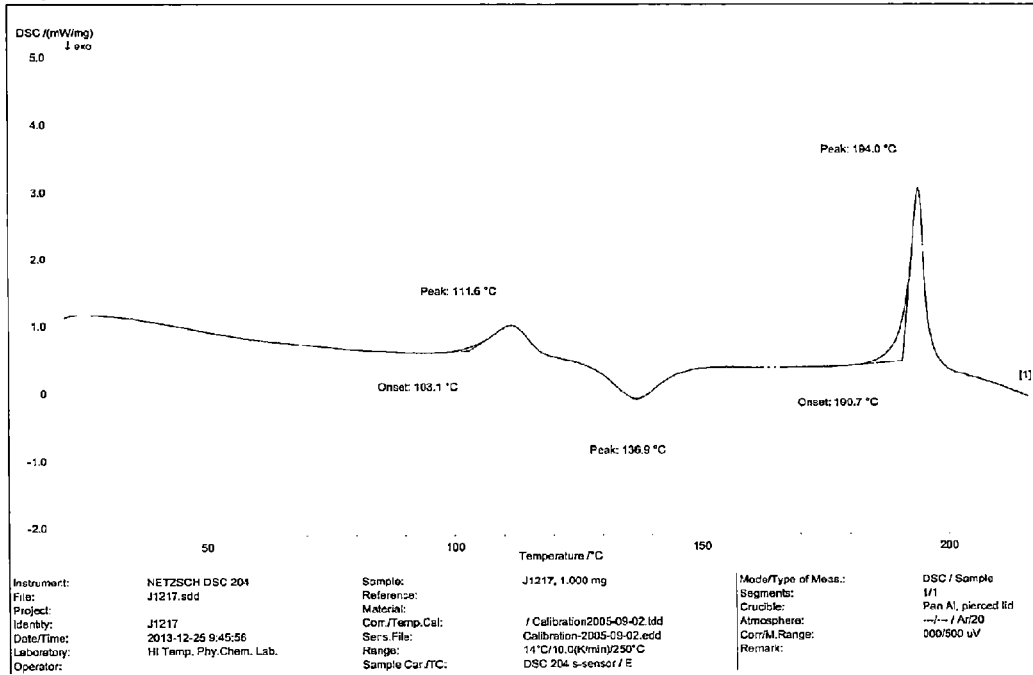
FIG. 2 shows a Differential Scanning calorimetry (DSC) thermogram of ivabradine hydrochloride.

The results of DSC test were shown in FIG. 2, and the DSC test indicated that the obtained S crystal form of ivabradine hydrochloride had crystal type transformation peaks including an endothermic characteristic peak at 111.6±1° C. and an exothermic characteristic peak at 136.9±1° C., and had a melting decomposition peak at 194±1° C.

Figure 3:
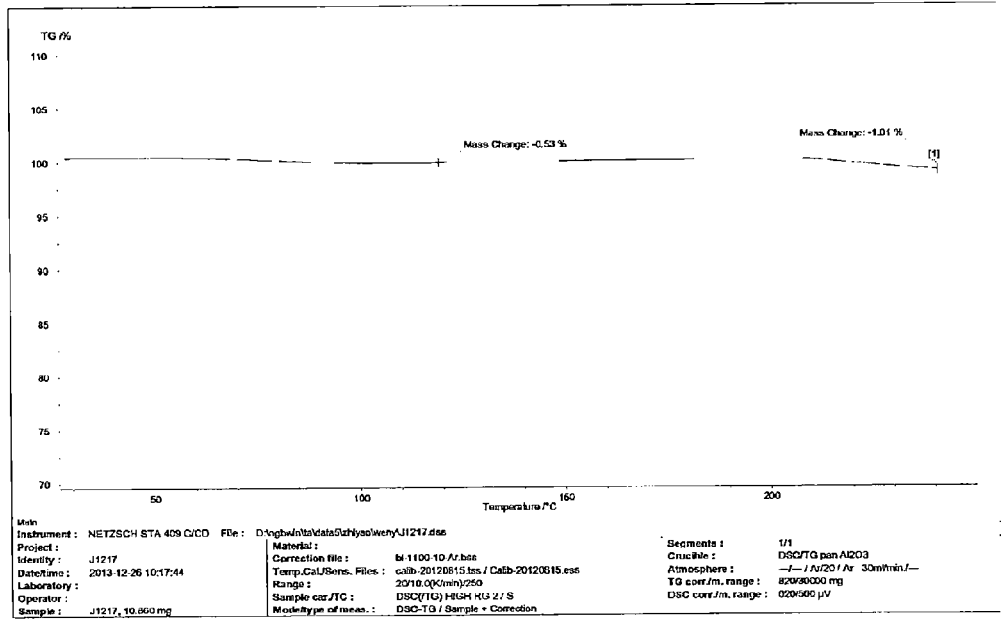
FIG. 3 shows a thermo-gravimetric (TG) curve of S crystal form of ivabradine hydrochloride.

The results of TG test were shown in FIG. 3, and the TG test further indicated that the obtained S crystal form of ivabradine hydrochloride gradually started to lose adsorption water at low temperature (about 60° C.). Compared with DSC thermogram, it's confirmed that the DSC thermogram had crystal type transformation peaks including an endothermic characteristic peak at 111.6±1° C. and an exothermic characteristic peak at 136.9±1° C., and had an endothermic peak at 194±1° C. as melting decomposition peak.

Example 2

10 g of ivabradine hydrochloride was added in 200 ml of acetonitrile, heated for dissolution under refluxing, and then stirred for 30 min, then naturally cooled to reach room temperature, crystallized at room temperature for 4 h, filtered and collected, dried under a reduced pressure at 50° C. for 12 h. 10 g wet product was obtained.

The moisture content of the wet product was 0.46%; the content of acetonitrile as residual solvent was 9.2%; the crystal form of which was identified as δ crystal form.

9.0 g of the above wet product was placed in 50 ml of tetrahydrofuran, controlled to have an internal temperature of 25-30° C., stirred to performed crystal type transformation for 24 h, the product was filtered out and collected, dried under a reduced pressure at 50° C. for 12 h to obtain 8.0 g product.

The product purity was measured as 99.88%; the content of the maximum single impurity was 0.02%; the measured moisture content of the product was 0.32%; the contents of residual solvents were as following: acetonitrile was not detected; the content of the residual THF was 0.001%; the product was identified as S crystal form via X-ray powder diffraction analysis.

Example 3

10 g of ivabradine hydrochloride was added in 200 ml of acetonitrile, heated for dissolution under refluxing, and then stirred for 30 min, then naturally cooled to reach room temperature, crystallized at room temperature for 4 h, filtered and collected, dried under a reduced pressure at 60° C. for 96 h. 9.0 g wet product was obtained.

The moisture content of the wet product was 0.12%; the content of acetonitrile as residual solvent was 0.015%; the crystal form of which was identified as δd crystal form.

9.0 g of the above wet product was placed in 50 ml of tetrahydrofuran, controlled to have an internal temperature of 25-30° C., stirred to performed crystal type transformation for 24 h, the product was filtered out and collected, dried under a reduced pressure at 50° C. for 24 h to obtain 8.0 g product.

The product purity was measured as 99.90%; the content of the maximum single impurity was 0.02%; the moisture content of product was measured as 0.12%; the contents of residual solvents were as following: acetonitrile was not detected; THF was not detected; the product was identified as S crystal form via X-ray powder diffraction analysis.

Example 4

10 g of ivabradine hydrochloride was added in 90 ml of acetone/ethanol (v/v=6:1) mixture solvent, heated for dissolution under refluxing, and then stirred for 30 min, then naturally cooled to reach room temperature, crystallized at room temperature for 4 h, filtered and collected, dried under a reduced pressure at 45° C. for 24 h. 10.0 g wet product was obtained.

The moisture content of the wet product was 0.42%; the contents of residual solvents were as following: the content of acetone was 0.2%; the content of ethanol was 0.30%; the crystal form of which was identified as δd crystal form.

9.0 g of the above wet product was placed in 50 ml of tetrahydrofuran, controlled to have an internal temperature of 25-30° C., stirred to performed crystal transformation for 24 h, the product was filtered out and collected, dried under a reduced pressure at 50° C. for 24 h to obtain 8.0 g product.

The product purity was measured as 99.92%; the content of the maximum single impurity was 0.02%; the moisture content of product was measured as 0.42%; acetone, ethanol and THF as residual solvents were all not detected; the product was identified as S crystal form via X-ray powder diffraction analysis.

Example 5: Humidity Stability Test

The S crystal form of ivabradine hydrochloride as prepared in Example 2 was spread on watch glass to form a thin layer and placed in the upper part of a desiccator, and saturated potassium carbonate solution was placed in the lower part of the desiccator, the humidity in the desiccator was detected (humidity: 43.1±0.5%), conditions were controlled at room temperature (20° C.) and constant humidity, and samples were taken at 1 h, 8 h, 16 h, 24 h, 48 h, 96 h for moisture and XRD tests, and the results are shown in the following table.

TABLE 3

|  | 1 h | 8 h | 16 h | 24 h | 48 h | 96 h |
|---|---|---|---|---|---|---|
| Moisture | 0.46% | 0.55% | 0.60% | 0.82% | 1.4% | 3.0% |
| Crystal form | S | S | S | S | S | S |

Conclusion: when the product was stored in open condition under certain humidity, it gradually and slowly absorbed water, but its crystal form did not change. Thus, when humidity was controlled to be lower than 43.1%±0.5% in storehouse, the product would not change in crystal form under sealed condition.

Example 6: High-Temperature Stability Test

TABLE 4

| | The 0$^{th}$ day | The 5$^{th}$ day | The 10$^{th}$ day |
|---|---|---|---|
| Properties | White crystalline powder, odorless, tasteless | White crystalline powder, odorless, tasteless | White crystalline powder, odorless, tasteless |
| Relevant substances Max single impurity | 0.04% | 0.05% | 0.05% |
| Total impurities | 0.19% | 0.20% | 0.20% |
| Crystal form | S | S | S |
| Content | 99.50% | 99.40% | 99.50% |

Conclusion: the high-temperature test at 60° C. showed that after the product was stored at 60° C. for 10 days, the indicators thereof, e.g. purity, did not change significantly in comparison with those at the 0$^{th}$ day, and the crystal form was very stable as well. Thus, the product could be stored stably in storehouse at room temperature.

Example 7

Medical prescription of 1000 tablets of 5 mg ivabradine hydrochloride tablet:

TABLE 5

| ivabradine hydrochloride | 5.39 g |
|---|---|
| Microcrystalline cellulose | 40 g |
| Anhydrous lactose | 60 g |
| colloidal silicon dioxide | 3 g |
| PVP K30 | 12 g |
| Magnesium stearate | 1 g |

What is claimed is:

1. An S crystal form of ivabradine hydrochloride, characterized in that the S crystal form of ivabradine hydrochloride has a powder diffraction pattern having characteristic peaks at degrees two-theta positions of 8.5±0.2, 11.5±0.2, 14.6±0.2, 15.3±0.2, 16.1±0.2, 17.1±0.2, 17.5±0.2, 17.8±0.2, 18.6±0.2, 19.3±0.2, 21.6±0.2, 21.9±0.2, 27.2±0.2.

2. The S crystal form of ivabradine hydrochloride according to claim 1, characterized in that the S crystal form of ivabradine hydrochloride has a DSC thermogram having an endothermic peak at 111.6±1° C., an exothermic peak at 136.9±1° C. and an endothermic peak at 194±1° C.

3. A method for preparing the S crystal form of ivabradine hydrochloride according to claim 1, comprising:
performing crystal type transformation by stirring a crystal form of ivabradine hydrochloride in tetrahydrofuran and filtering and collecting, drying under a reduced pressure to obtain the S crystal form of ivabradine hydrochloride;
the crystal form of ivabradine hydrochloride is δ crystal form or δd crystal form of ivabradine hydrochloride;
the ratio of mass (g) of the crystal form of ivabradine hydrochloride or amorphous form of ivabradine hydrochloride to volume (ml) of tetrahydrofuran is 1:3 to 1:6 (g/ml);
the stirring is performed at a temperature of 0-50° C.; and the stirring is performed for 6-72 h.

4. A pharmaceutical composition, comprising an effective amount of the S crystal form of ivabradine hydrochloride according to claim 1, and optionally one or more pharmaceutically acceptable carriers.

5. The pharmaceutical composition according to claim 4, having a preparation form of tablet, orally disintegrating tablet, dispersible tablet, sustained and controlled release tablet, capsule or sustained and controlled capsule.

6. The method according to claim 3, wherein the stirring is performed at a temperature of 25-30° C.

7. The method according to claim 3, wherein the stirring is performed for 12-24 h.

* * * * *